United States Patent
Suh et al.

(10) Patent No.: US 6,528,628 B1
(45) Date of Patent: Mar. 4, 2003

(54) ERYTHROMYCIN A COMPOUNDS AND PROCESS FOR PREPARING THE SAME

(75) Inventors: Kwee-Hyun Suh, Kyunggi-do (KR); Nam-Du Kim, Kyunggi-do (KR); Hyoung-Jun Pae, Kyunggi-do (KR); Gwan-Sun Lee, Seoul (KR)

(73) Assignee: Hanmi Pharmaceutical Co., Ltd., Kyunggi-do (KR)

( * ) Notice: Subject to any disclaimer, the term of this patent is extended or adjusted under 35 U.S.C. 154(b) by 0 days.

(21) Appl. No.: 09/869,559

(22) PCT Filed: Dec. 27, 1999

(86) PCT No.: PCT/KR99/00824

§ 371 (c)(1),
(2), (4) Date: Jun. 29, 2001

(87) PCT Pub. No.: WO00/39142

PCT Pub. Date: Jul. 6, 2000

(30) Foreign Application Priority Data

Dec. 29, 1998 (KR) .......................................... 98-60263

(51) Int. Cl.$^7$ .......................... C07H 1/00; C07H 17/08
(52) U.S. Cl. ........................ 536/7.4; 536/7.2; 536/18.5
(58) Field of Search ......................... 536/7.2, 7.4, 18.5

(56) References Cited

FOREIGN PATENT DOCUMENTS

| EP | A 260938 | 3/1988 |
|----|----------|--------|
| JP | A 6281399 | 4/1987 |
| JP | A 6287599 | 4/1987 |
| JP | A 0276893 | 3/1990 |

*Primary Examiner*—Elli Peselev
(74) *Attorney, Agent, or Firm*—Birch, Stewart, Kolasch & Birch, LLP

(57) ABSTRACT

A new erythromycin A 9-oxime compound which can be effectively used as intermediates for the preparation of erythromycin A oxime compound, a process for preparing the same and a process for preparing 6-O-alkyl erythromycin A or its oxime using the same is described.

14 Claims, No Drawings

ERYTHROMYCIN A COMPOUNDS AND PROCESS FOR PREPARING THE SAME

This application is the national phase under 35 U.S.C. §371 of PCT International Application No. PCT/KR99/00824 which has an International filing date of Dec. 27, 1999, which designated the United States of America and was not published in English.

TECHNICAL FIELD

The present invention relates to a new erythromycin A 9-oxime compound which can effectively be used as an intermediate for the preparation of 6-O-alkyl erythromycin A such as 6-O-methyl erythromycin A (hereinafter referred to as "clarithromycin") or its oxime, a process for preparing the same and a process for preparing 6-O-alkyl erythromycin A or its oxime using the same.

BACKGROUND ART

6-O-alkyl erythromycin A is a semi-synthetic macrolide antibacterial agent showing an excellent antibacterial activity against a number of bacteria which can cause diseases in human or mammals, for example, gram-positive bacteria, a part of gram-negative bacteria, anaerobic bacteria, Mycoplasma, and Chlamidia, etc., and also can be used as a raw material for the synthesis of other antibiotic in this field, and it therefore is a pharmaceutically important material.

6-O-alkyl erythromycin A compound including 6-O-methyl erythromycin A can be prepared by selectively alkylating the 6-position of suitably protected erythromycin A 9-oxime, eliminating the protecting groups and then carrying out deoximation. Since erythromycin A 9-oxime has a number of reactive hydroxy groups including the hydroxy group of oxime and a dimethylamino group at the 3' position which can also participate in alkylation, it is very important to carry out alkylation of the hydroxy group at the 6 position after protecting these groups with suitable substituents.

Prior art processes for preparing 6-O-alkyl erythromycin A, especially 6-O-methyl erythromycin A from erythromycin A 9-oxime are disclosed in EP patent Nos. 0,158,467, 0,195,960, and 0,272,110 and U.S. Pat. No. 5,719,272 and WO 97/36913.

Separately from the above processes, processes for preparing it from erythromycin A derivatives are disclosed in EP Patent Nos. 0,147,062 and 0,177,696, but these are not practical.

Known processes for preparing 6-O-alkyl erythromycin A compound from erythromycin A 9-oxime can be summarized as follows:

(1) The first method comprises protecting oxime hydroxy group of erythromycin A 9-oxime with an alkyl group, etc. and protecting the hydroxy group at the 2' position and dimethylamino group at the 3' position with benzyloxycarbonyl groups, thereafter carrying out alkylation such as methylation of the hydroxy group at the 6 position.

However, this process has some problems in industrial use since benzyloxycarbonyl chloride used as the protecting group is expensive and must be used in an excess amount. Furthermore, it has a drawback that it requires an additional step for regenerating the dimethylamino group at the 3' position after carrying out alkylation of the hydroxy group at the 6 position.

(2) The second process comprises protection of the oxime hydroxy group and the hydroxy group at the 2' position of erythromycin A 9-oxime with benzyl groups, together with quarternization of the dimethylamino group at the 3' position with the same protecting group, and then alkylation of the hydroxy group at the 6 position.

However, this process has a drawback that, after carrying out alkylation of the hydroxy group at the 6 position, the protecting group at the 2' position is not readily removed in the step of deprotection of the benzyl group by hydrogenation due to catalytic poison phenomenon.

(3) The third process comprises protection of the oxime hydroxy group of erythromycin A 9-oxime with a ketal compound such as cyclohexanone diisopropyl ketal, protection of the hydroxy groups at the 2' and 4' positions with silyl groups, and then carrying out alkylation of the hydroxy group at the 6 position. This process has advantages that it does not require protection of the dimethylamino group at the 3' position, and it is possible to eliminate the protecting groups at one time after carrying out alkylation. However, it has a drawback that ketal compounds which are used in protecting the hydroxy group of oxime should be separately synthesized.

(4) The fourth method comprises carrying out protection of all of the oxime hydroxy group and the hydroxy groups at the 2' and 4' positions of erythromycin A 9-oxime with silyl groups, and then carrying out alkylation of the hydroxy group at the 6 position. However, this process has a number of drawbacks that since the silyl group is quite unstable as the protecting group for oxime, the hydroxy group of oxime is also alkylated during the alkylation reaction for the hydroxy group at the 6 position.

DISCLOSURE OF INVENTION

Therefore, the present inventors have extensively conducted a research in order to solve the above mentioned drawbacks involved in the prior art techniques and to prepare 6-O-alkyl erythromycin A in a high yield. As a result, we found that 6-O-alkyl erythromycin A of the general formula (II) and its oxime can conveniently be prepared in a high yield with low cost by a process wherein two molecules of the hydroxy groups of erythromycin A 9-oxime is first protected with one molecule of protecting group using the protecting groups which can react with oxime at two positions to give a erythromycin A 9-oxime compound in symmetric structure; and then up to four hydroxy groups of erythromycin A 9-oxime compound corresponding to the 2' and 4" positions of erythromycin A are protected with silyl protecting groups; and the hydroxy group at the 6 position is selectively alkylated; and finally deprotection and deoximation are carried out.

(II)

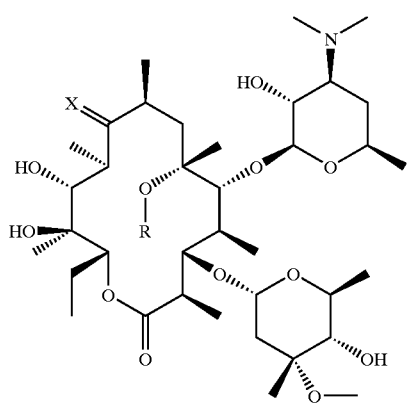

wherein,
R represents hydrogen or a $C_{1-3}$ alkyl group; and
X represents O or N—OH.

BEST MODE FOR CARRYING OUT THE INVENTION

The present invention provides a process for preparing 6-O-alkyl erythromycin A 9-oxime and 6-O-alkyl erythromycin A represented by the following formula (II) which comprises the steps (a) to (e):

(a) reacting erythromycin A 9-oxime represented by the following formula (III) with a bifunctional linker represented by the following formula (IV) to give an erythromycin A 9-oxime compound represented by the following formula (V);

(b) silylating the erythromycin A 9-oxime compound of formula (V) obtained in the step (a) to give an erythromycin A 9-oxime compound represented by the following formula (VI);

(c) alkylating the compound of formula (VI) obtained in the step (b) to give an erythromycin A 9-oxime compound represented by the following formula (VII);

(d) desilylating the erythromycin A 9-oximie compound of formula (VII) obtained in step (c) to give an erythromycin A 9-oxime compound represented by the following formula (VIII); and (e) removing the oxime protecting group of the compound of formula (VIII) obtained in the step (d) or consecutively carrying out removal of the oxime protecting group and deoximation reaction:

(II)

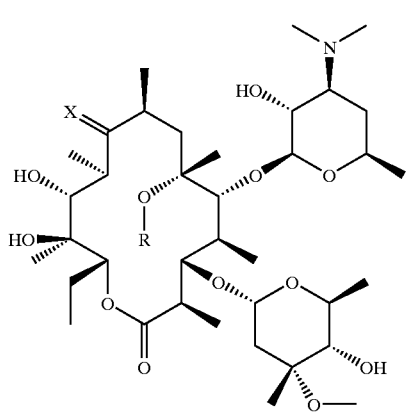

(III)

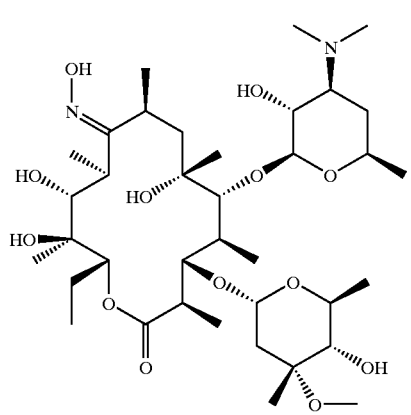

(IV)

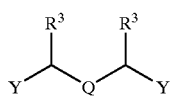

(V)

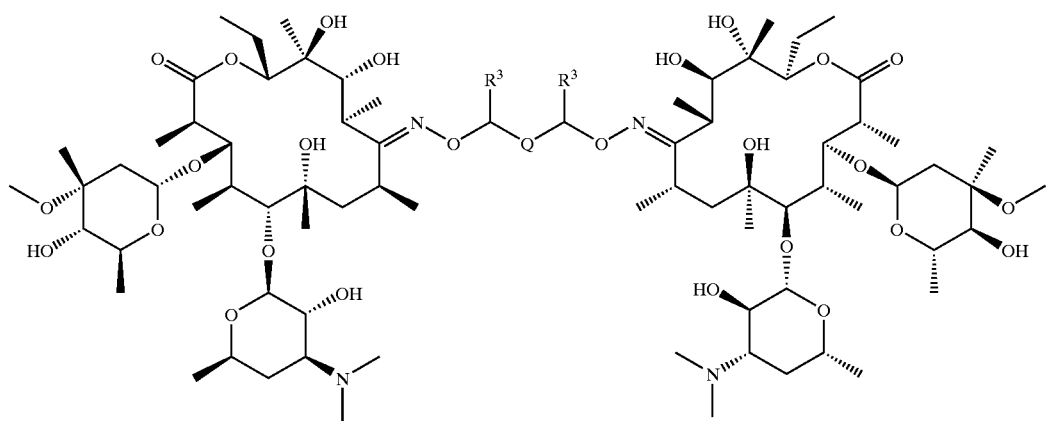

(VI)

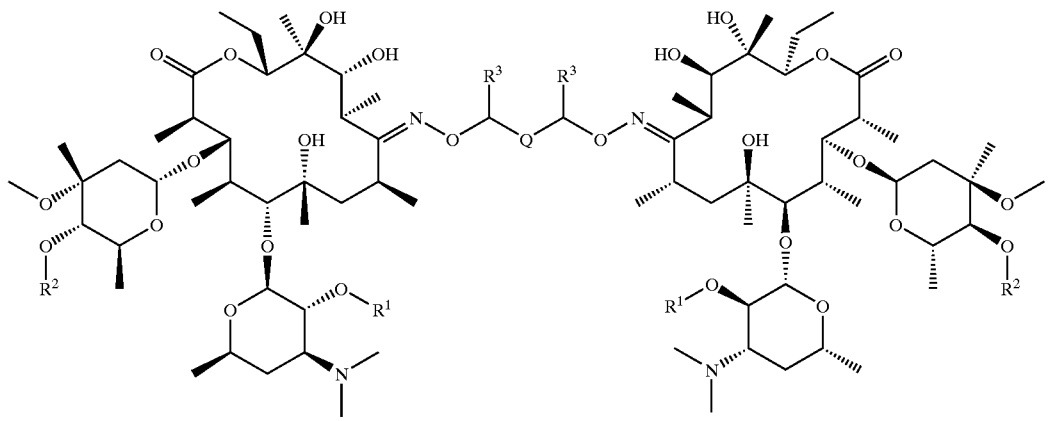

(VII)

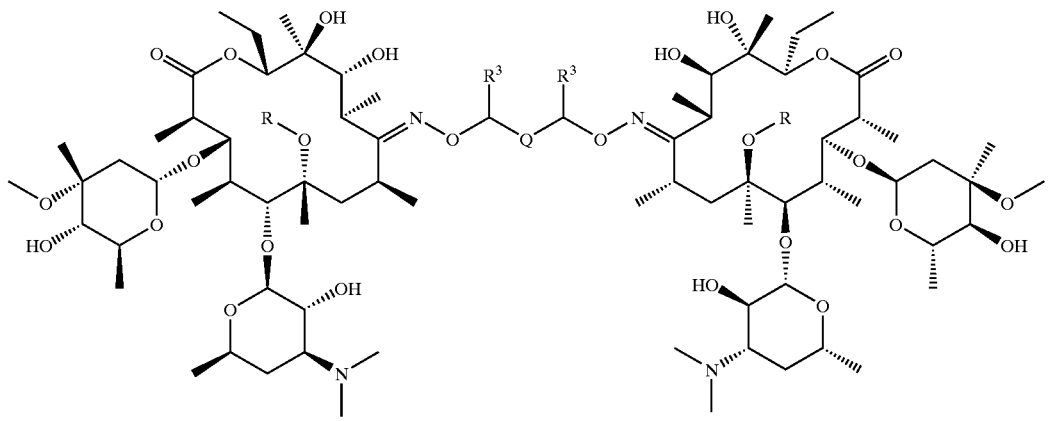

(VIII)

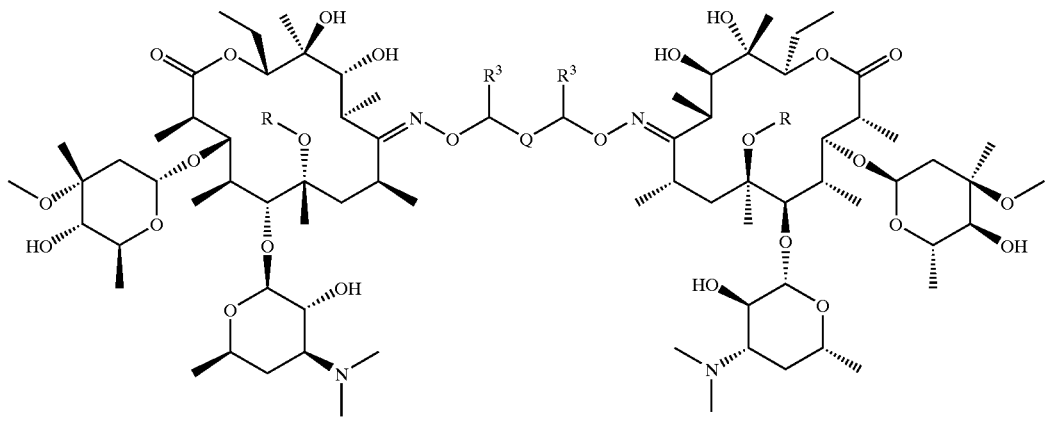

wherein,

R represents a $C_{1-3}$ alkyl group;

$R^1$ and $R^2$ each independently represents a silyl group represented by $-SiR^4R^5R^6$ which $R^4$, $R^5$, and $R^6$ each independently represents a $C_{1-6}$ alkyl group, a $C_{1-3}$ alkyl group substituted with a phenyl group, a phenyl group, a $C_{5-7}$ cycloalkyl group, or a $C_{2-5}$ alkenyl group; or $R^2$ represents hydrogen;

$R^3$ represents hydrogen, a 1-alkenyl group, or an aryl group;

Q represents a cis- or trans-alkenylene group represented by $-(CH=CH)_m-$, a α,ω-dienylene group represented by $-[CH=CH-(CH_2)_m-CH=CH]-$, a phenyl group consisting of ortho-, meta- or para-, etc., an arylene group such as naphthalenyl, anthracenyl or pyridinyl group, etc. or an alkylene group represented by $-(CH_2)_n-$ when $R^3$ represents a 1-alkenyl group or an aryl group, m is an integer of 1 to 3, and n is an integer of 1 to 10, wherein one or more hydrogens in the above alkylene group, alkenylene group, dienylene group or arylene group may be substituted with a suitable alkyl substituent;

X represents O or N—OH; and

Y represents a leaving group such as chloride, bromide, iodide, mesylate, tosylate and triflate.

The present invention also provides an erythromycin A 9-oxime compound represented by the following formula (I) which can be used as an intermediate for the preparation of 6-O-alkyl erythromycin A 9-oxime and 6-O-alkyl erythromycin A represented by the formula (II).

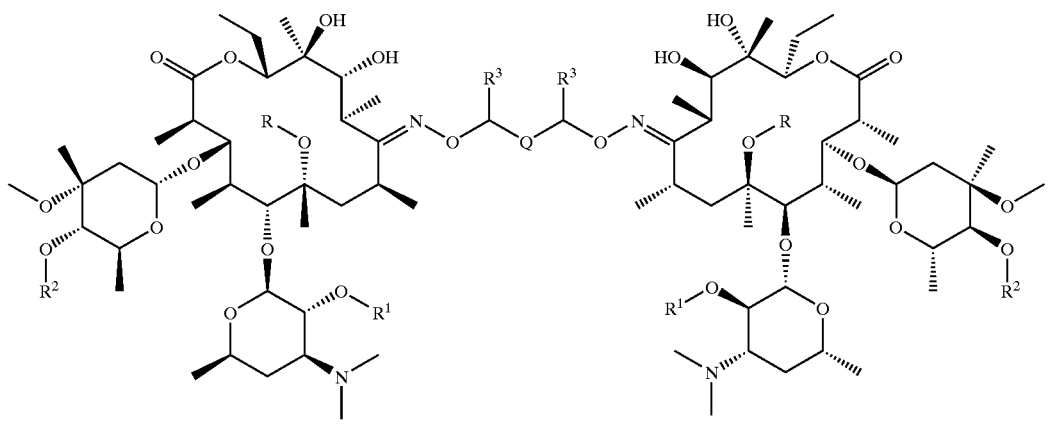

(I)

wherein,

R represents hydrogen, or a $C_{1-6}$ alkyl group, $R^1$ and $R^2$ each independently represents hydrogen or a silyl group represented by —SiR$^4$R$^5$R$^6$ in which R$^4$, R$^5$, and R$^6$ each independently represents a $C_{1-6}$ alkyl group, a $C_{1-3}$ alkyl group substituted with a phenyl group, a phenyl group, a $C_{5-7}$ cycloalkyl group, or a $C_{2-5}$ alkenyl group; or $R^3$ represents hydrogen, a 1-alkenyl group, or an aryl group;

Q represents a cis- or trans-alkenylene group represented by —(CH=CH)$_m$—, a α,ω-dienylene group represented by —[CH=CH—(CH$_2$)$_m$—CH=CH]—, a phenyl group consisting of ortho-, meta- or para-, etc., an arylene group such as naphthalenyl, anthracenyl or pyridinyl group, etc. or an alkylene group represented by —(CH$_2$)$_n$— when $R^3$ represents a 1-alkenyl group or an aryl group, m is an integer of 1 to 3, and n is an integer of 1 to 10, wherein one or more hydrogens in the above alkylene group, alkenylene group, dienylene group or arylene group may be substituted with a suitable alkyl substituent.

Hereinafter, the invention will be illustrated in more detail.

Erythromycin A 9-oxime compound represented by the formula (I) according to the present invention is an intermediate in which two molecules of erythromycin A 9-oxime is connected to a specific group of the bifunctional linker serving as a protecting group of oxime. Using this compound, the desired 6-O-alkyl erythromycin A and its oxime of formula (II) can be conveniently prepared in a high yield.

In the erythromycin A 9-oxime compound of formula (I) according to the present invention, preferred are those in which Q represents a 1,2-diphenylethyl group, a phenyl group consisting of ortho-, meta- or para-, a 1,4-naphthalenyl group, a cis- or trans-ethylene group or a butadienyl group; R represents hydrogen or a methyl group; $R^1$ represents a trimethyl silyl group, $R^2$ represents hydrogen or a trimethylsilyl group; and $R^3$ represents hydrogen.

In the erythromycin A 9-oxime compound of formula (I) according to the present invention, more preferred are those in which Q represents a para-phenyl group; R represents a methyl group; $R^1$ represents a trimethylsilyl group, $R^2$ represents hydrogen or trimethylsilyl group; and $R^3$ represents hydrogen.

The term used herein, "alkyl" includes an alkyl group having carbon number of 1 to 3.

According to the present invention, the process for preparing 6-O-alkyl erythromycin A and its 9-oxime represented by the formula (II) via an erythromycin A 9-oxime compound represented by the formula (I) from the erythromycin A 9-oxime of formula (III) can be accomplished by separately conducting several reaction steps or consecutively or concurrently conducting two or more necessary reaction steps without isolating the desired products in each step. Therefore, the present invention encompasses the two methodologies which will be explained in more detail.

Step (a)

In this step, erythromycin A 9-oxime of formula (III) is reacted with bifunctional linker of formula (IV) in a solvent under the presence of a base to give an erythromycin A 9-oxime compound represented by the formula (V).

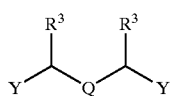

(IV)

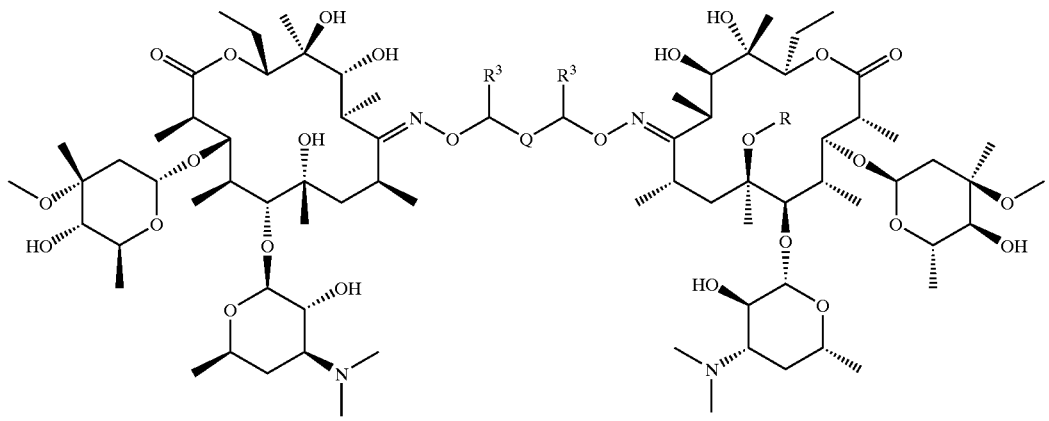

(V)

wherein,

R³ represents hydrogen, a 1-alkenyl group or an aryl group;

Q represents a cis- or trans-alkenylene group represented by —(CH=CH)$_m$—, a α,ω-dienylene group represented by —[CH=CH—(CH$_2$)$_m$—CH=CH]—, a phenyl group consisting of ortho-, meta- or para-, etc., an arylene group such as naphthalenyl, anthracenyl or a pyridinyl group, etc., or an alkylene group represented by —(CH$_2$)$_n$— when R³ represents a 1-alkenyl group or an aryl group, m is an integer of 1 to 3, n is an integer of 1 to 10, wherein one or more hydrogens in the above alkylene group, alkenylene group, dienylene group or arylene group may be substituted with a suitable alkyl substituent; and Y represents a leaving group such as chloride, bromide, iodide, mesylate, tosylate and triflate.

The bifunctional linker represented by the formula (IV) which can be used in the step (a) includes, for example, an aryl substituted alkyl group such as 1,2-dibromo-1,2-diphenylethane, an alkenyl group such as 1,4-dichloro-2-butene, and an aryl group such as α,α'-dichloro-o-xylene, α,α'-dichloro-m-xylene, α,α'-dichloro-p-xylene, 2,4-bis(chloromethyl)-1,3,5-trimethylbenzene, 2,6-bis(chloromethyl)pyridine etc. It is preferable to employ this bifunctional linker in an amount of about 0.5 mole equivalent for erythromycin A 9-oxime.

As the solvent used in the step (a), preferred are aprotic polar solvent or the mixture thereof such as acetone, acetonitrile, 1,2-dimethoxyethane, tetrahydrofuran, 1,4-dioxane, N,N-dimethylformamide, N,N-dimethylacetamide, dimethylsulfoxide, sulfolane, N,N,N',N',N'',N''-hexamethylphosphoramide, etc. Also, as the base, for example, sodium hydride, potassium hydride, sodium hydroxide, potassium hydroxide, potassium t-butoxide, sodium carbonate, potassium carbonate, etc. may be preferably used. It is sufficient to use the base in an amount of about 1 to 1.5 mole equivalents for erythromycin A 9-oxime. The reaction is carried out at about −15° C. to 50° C., preferably 0° C. to room temperature under stirring. After completion of the reaction, reactants are dispersed into water and then the resulting solid is filtered and dried to give the desired product (V) conveniently.

The erythromycin A 9-oxime of formula (III) which is reacted with the bifunctional linker of formula (IV) according to the present invention may be present as two 'syn' form and 'anti' form isomers. The isomer in the present invention may be any of them or a mixture thereof, with anti-form isomer being preferred.

Step (b)

The erythromycin A 9-oxime compound represented by the above formula (V) is reacted with various silylating agents to prepare an erythromycin A 9-oxime compound represented by the formula (VI) in which two hydroxy groups at the 2' position and two hydroxy groups at the 4'' position of the above formula (V) corresponding to the 2' and 4' positions of erythromycin A are protected with silyl groups.

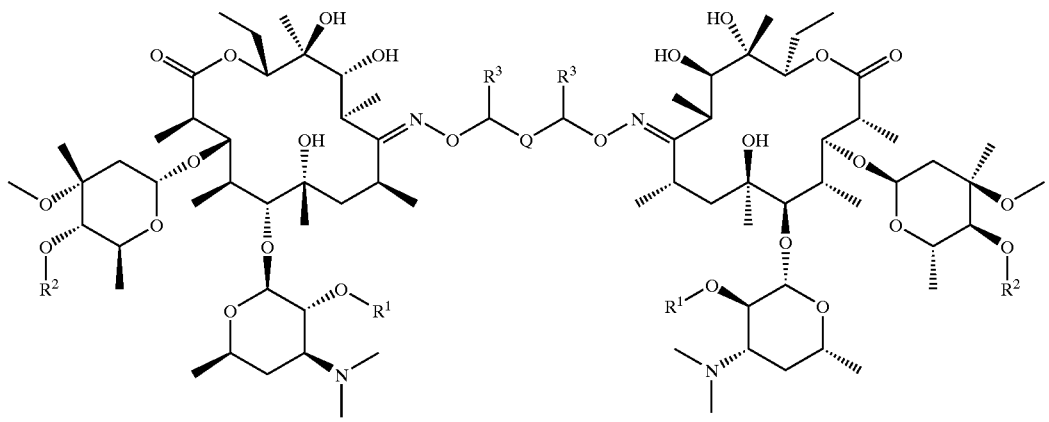

(VI)

wherein,

Q and $R^3$ are as defined above, $R^1$ and $R^2$ each independently represents a silyl group represented by —$SiR^4R^5R^6$ in which $R^4$, $R^5$, and $R^6$ each independently represents a $C_{1-6}$ alkyl group, a $C_{1-3}$ alkyl group substituted with a phenyl group, a phenyl group, a $C_{5-7}$ cycloalkyl group, or a $C_{2-5}$ alkenyl group; or $R^2$ represents hydrogen.

The examples of the silylating agent for the compound of formula (V) include chlorosilanes such as Step (c)

The erythromycin A 9-oxime compound represented by the formula (VI) is reacted with various alkylating agents to prepare an erythromycin A 9-oxime compound represented by the following formula (VII) in which two hydroxy groups of the compound of formula (VI) corresponding to the 6 position of erythromycin A are alkylated.

(VII)

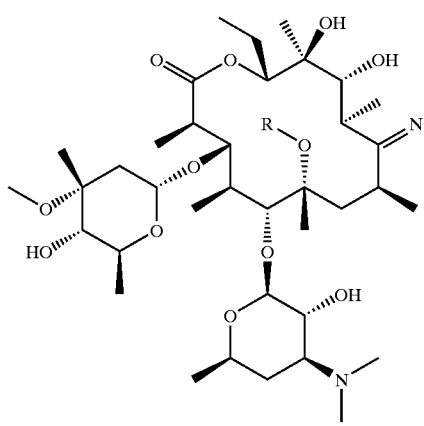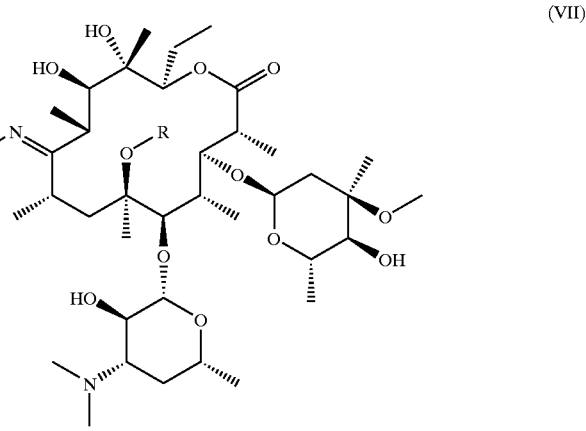

trimethylchlorosilane, triethylchlorosilane, and tert-butyldimethylchlorosilane; silylamines such as 1,1,1,3,3,3-hexamethyldisilazane, trimethylsilylimidazole, and N,N-dimethylaminotrimethylsilane; and silylamides such as bis(trimethylsilyl)acetamide, trimethylsilyl diphenylurea, and bis(trimethylsilyl)urea, etc. When chlorosilanes are used, it is desirable to carry out the reaction under the presence of a base, examples of which include inorganic base such as sodium hydroxide, potassium hydroxide, sodium carbonate, potassium carbonate, sodium bicarbonate, potassium bicarbonate and organic base such as trimethylamine, triethylamine, tri-n-butylamine, diisopropylethylamine, pyridine, N,N-dimethylamine, imidazole, 1,8-diazabicyclo[5,4,0]undec-7-ene, etc. When silylamines are used, it is preferable to use together with a weak acid salt such as ammonium chloride, pyridine hydrochloride, pyridine p-toluenesulfonate, etc. The amount of silylating agent to be used is about 2 to 20 mole equivalents with respect to the compound of formula (V). The reaction is coined out at 0° C. to reflux temperature of the solvent, preferably at about 10° C. to 50° C. in a solvent under stirring. As the solvent, dichloromethane, 1,2-dichloroethane, chloroform, acetone, acetonitrile, tetrahydrofuran, dioxane, 1,2-dimethoxymethane, N,N-dimethylformamide, N,N-dimethylacetamide, dimethyl sulfoxide, etc. can be used. Depending upon the kind and amount of the silylating agent to be used in the step (b), it is possible to silylate only two hydroxy groups of the compound of formula (V) which corresponds to the 2' position of erythromycin A or to silylate the two hydroxy groups of the compound of formula (V) which correspond to the 2' position and any of the two hydroxy groups of the compound of formula (V) which correspond to the 4" position of erythromycin A.

In preparing the compound of formula (VI) according to the present invention, it is possible to consecutively carry out the reaction steps (a) and (b) from the compound of formula (II) in the same vessel without isolating the compound of formula (V).

wherein.

Q $R^1$, $R^2$ and $R^3$ are as defined above, and R represents a $C_{1-3}$ alkyl group.

The reaction of the compound of formula (VI) and the alkylating agent is carried out at −15° C. to 40° C., preferably about 0° C. to room temperature under the presence of a base in a solvent under stirring. As the alkylating agent, methyl bromide, methyl iodide, ethyl bromide, ethyl bromide, ethyl iodide, propyl bromide, propyl iodide, allyl bromide, dimethyl sulfate, p-toluenesulfonylmethane, methanesulfonylmethane, etc. can be used. The amount of alkylating agent to be used is about 2 to 4 mole equivalents with respect to the compound of formula (VI). The solvent which can be used in this reaction includes aprotic polar solvents such as N,N-dimethylformamide, N,N-dimethylacetamide, N-methyl-2-pyrolidone, dimethyl sulfoxide, N,N,N',N',N",N"-hexamethylphosphoramide, etc. and the mixture thereof or a mixed solvent consisting of one solvent selected from the above aprotic solvent and another solvent selected from the group consisting of tetrahydrofuran, 1,2-dimethoxyethane, dioxane, acetonitrile, etc. As the base, sodium hydride, potassium hydride, sodium hydroxide, potassium hydroxide, potassium t-butoxide, etc. may be used. The base is used in an amount of about 2 to 4 mole equivalents with respect to the compound of formula (VI).

It is well known that when alkylating two hydroxy groups of formula (VI) corresponding to the 6 position of erythromycin A according to the present invention, the condition required for preventing 3'-dimethylamino group from becoming a quarternary salt is generally to protect the 2'-hydroxy group with a silyl group and the protection of 4"-hydroxy group with a silyl group is not an essential condition. Upon alkylation reaction of the two hydroxy groups at the 6 position of formula (VI) according to the present invention, N-methylation hardly occurs at the two 3'-dimethylamino groups of formula (VI). Therefore, the protection of the two 3'-dimethylamino groups is not required.

Step (d)

The erythromycin A 9-oxime compound represented by the formula (VII) may be converted into an erythromycin A 9-oxime compound represented by the formula (VIII) by removing silyl groups which are up to 4 hydroxy protecting groups corresponding to the 2' and 4" positions of erythromycin A.

(diphenyl)-phosphine, etc. may be used. Typically, a combined catalyst of palladium and triphenylphosphine is used. This reaction may be carried out in formic acid or the salt thereof. As the example of the salt, ammonium salts such as ammonium formate, trimethylammonium formate or alkali metal salts such as sodium formate, potassium formate, etc. may be listed.

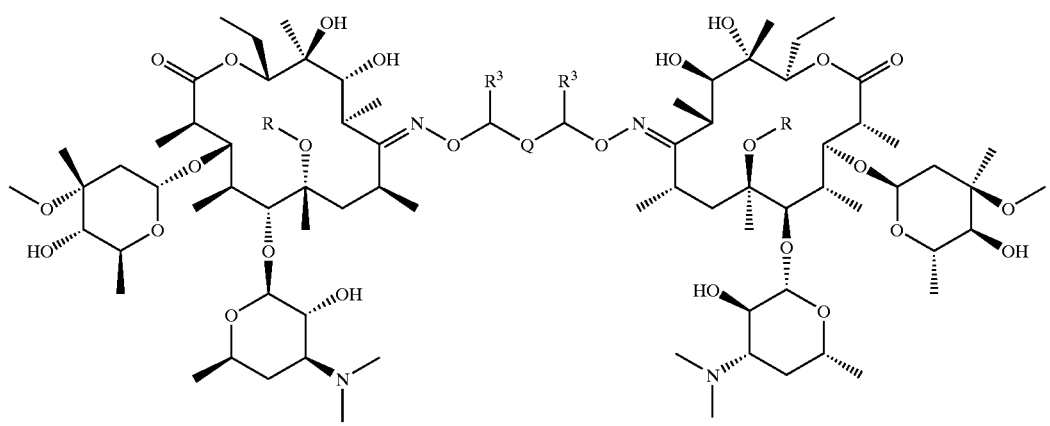

(VIII)

wherein,

Q and $R^3$ are as defined above, and R is a $C_{1-3}$ alkyl group.

Generally, the method for removing silyl groups serving as the hydroxy protecting groups of hydroxy group is well known. For example, this protecting group can be readily removed by treating with an organic acid such as formic acid or an inorganic acid such as hydrochoric acid in an organic solvent such as alcohols or in a mixed solvent of water and the organic solvent or by tetrabutylammonium fluoride, etc. in an organic solvent such as tetrahydrofuran.

Step (e)

6-O-alkyl erythromycin A 9-oxime represented by the formula (II) in which X represents N—OH can be prepared from the compound of formula (VIII) obtained in step (d) by removing oxime protecting groups of two molecules of 6-O-alkyl erythromycin A 9-oximes.

Removal of the protecting groups which protect two oximes in the compound of formula (VIII) can easily be carried out by reductive hydrogenation reaction of homogeneous or heterogeneous system. For example, this reaction can be carried out in alcohols such as methanol, ethanol, etc. or in an aqueous solution of alcohols under the presence of palladium or palladium-carbon catalyst under hydrogen atmosphere with stirring. At this time, it may be possible to add formic acid, acetic acid, etc. in order to prevent catalyst poison due to the nitrogen atom of 3'-dimethylamino group and to easily carry out the reaction.

The reaction may also be carried out in methanol, ethanol, and N,N-dimethylformamide using ammonium formate, sodium formate or the mixture of the formate with formic acid which serves as the hydrogen source under the presence of palladium or palladium-carbon catalyst at room temperature to 100° C. with stirring.

This reaction can also be carried out using a suitable catalyst in transition elements of VIIIB group or a catalyst consisting of the elements and a suitable ligand. As the example of transition elements, ruthenium, rhodium, palladium and platinum may be listed. The catalyst can be used as a salt or a complex. As the ligand, triphenylphosphine, tri-n-butylphosphine, triethylphosphite, 1,2-ethylene In addition to the above process in which the oxime protecting functional groups are removed from the compound of formula (VIII) to prepare 6-O-alkyl erythromycin A 9-oxime represented by the formula (II) in which X represents N—OH, the compound of formula (II) may be prepared starting from the compound of formula (VII) by concurrently carrying out the steps of (d) and (e). The same hydrophilic solvent as used in the steps (d) and (e) may be used in these reactions. In these reactions, the order of the removal of substituents $R^1$ and $R^2$ and the removal of the oxime protecting functional groups may be reversed.

The thus obtained 6-O-alkyl erythromycin A 9-oxime of formula (II) in which X represents N—OH can be deoximized in accordance with the known process, for example, as disclosed in EP Nos. 0,158,467 and 0,195,960, using inorganic oxidized sulfur compounds such as sodium hydrogen sulfite, sodium pyrothiosulfate, sodium thiosulfate, sodium hydrosulfite, sodium metabisulfite, sodium dithionate, potassium hydrogen sulfite, potassium thiosulfate, potassium metabisulfite, trichlorotitanium-ammonium acetate, sodium nitrite-hydrochloric acid, etc. to prepare 6-O-alkyl erythromycin A of formula (II) in which X represents O.

According to the present invention, however, in order to shorten the reaction steps and to efficiently prepare 6-O-alkyl erythromycin A of formula (II) in which X represents O, it is possible to concurrently or consecutively carry out the desilylation reaction of the step (d) from the compound of formula (VII), the removal of oxime protecting groups in step (e) and the deoximation reaction, or if is also possible to concurrently or consecutively carry out deprotection reaction of oxime protecting groups in step (e) from the compound of formula (VIII) and deoximation reaction. The same hydrophilic solvent as used in the steps (d) and (e) may be used in these reactions. For example, the compound of formula (VII) is reacted with formic acid, ammonium formate, palladium-carbon and sodium hydrogen sulfite in methanol, ethanol or an aqueous solution thereof at 50° C. to the refluxing temperature of solvent to prepare 6-O-alkyl erythromycin A of formula (II) including the commercial antibiotic, 6-O-methyl erythromycin A. The amount of formic acid to be used is about 10 to 100 mole equivalents, preferably, about 20 to 50 mole equivalents and the amount of ammonium formate is about 2 to 20 mole equivalents, preferably about 4 to 10 mole equivalents with respect to the compound of formula (VII). Palladium is used in an amount of about 0.01 to 0.5 mole equivalents in the standard of 1% to 20% regardless of content of moisture. The amount of sodium hydrogen sulfite is about 2 to 30 mole equivalents, preferably about to 8 to 20 mole equivalents.

The compounds represented by the formulas (V), (VI), (VII) and (VIII) which provided in order to illustrate each reaction step according to the present invention are encompassed by the compound of formula (I) in their scope. Therefore, it is apparent that the compounds of formulas (V), (VI), (VII) and (VIII) are encompassed by the compound of formula (I).

Hereinafter, the invention will be explained in more detail by way of the following examples. However, it is apparent that the scope of the invention shall not be limited by the examples.

EXAMPLE 1

21.3 G of erythromycin A 9-oxime were dissolved into 70 ml of N,N-dimethylformamide and cooled to 0 to 5° C. Then, 2.50 g of α,α'-dichloro-p-xylene and 1.94 g of potassium hydroxide in powder were added thereto. The mixture was stirred for three hours at 0 to 5° C. and for 15 hours at room temperature, and the reactants were then poured in excess of water. The thus precipitated solids were filtered, washed with water, and dried to give, 22.8 g (yield: 100%) of α,α'-bis(erythromycin A 9-oxime)-9-O-p-xylene as white powder. This was purified by recrystalization from ethanol, and centrifugation.

PMR (CDCl$_3$, ppm) δ7.33(s, 4H, —C$_6$H$_4$—), 5.07(s, 4H, two benzyl —CH$_2$—), 3.32(s, 6H, two cladinose —OCH$_3$), 2.29(s, 12H, two desosamine —N(CH$_3$)$_2$)

EXAMPLE 2

After 22.4 g of α,α'-bis(erythromycin A 9-oxime)-9-O-p-xylene prepared in Example 1 were dissolved in 140 ml of N,N-dimethylformamide, 2.24 g of ammonium chloride and 25 ml of 1,1,1,3,3,3-hexamethyldisilazane were added to the solution. The mixture was stirred for 2 hours at 35 to 40° C. and then cooled to room temperature. After addition of 300 ml of n-hexane, the solution was washed with water and then brine in order. The organic phase was dried over magnesium sulfate and the solvent was concentrated under reduced pressure to give 26.4 g (yield: 100%) of α,α'-bis[2',4"-O-bis(trimethylsilyl)erythromycin A 9-oxime]-9-O-p-xylene in foam. The analytical sample was purified by silica gel column chromatography (eluent, hexane/acetone=4/1).

PMR (CDCl$_3$, ppm) δ7.32(s, 4H, —C$_6$H$_4$—), 5.07(s, 4H, two benzyl —CH$_2$—), 3.31(s, 6H, two cladinose —OCH$_3$), 2.23(s, 12H, two desosamine —N(CH$_3$)$_2$, 0.16(s, 18H, two —Si(CH$_3$)$_3$, 0.10(s, 18H, two —Si(CH$_3$)$_3$)

EXAMPLE 3

After 7.49 g of erythromycin A 9-oxime were dissolved in 25 ml of N,N-dimethylformamide, the solution was cooled to 0 to 5° C. Then, 0.88 g of α,α'-dichloro-p-xylene and 6.88 g of potassium hydroxide in powder were added thereto. The mixture was stirred for 3 hours at 0 to 5° C. and then 13 hours at room temperature. 25 ml of N,N-dimethylformamide, 0.80 g of ammonium chloride and 11 ml of 1,1,1,3,3,3-hexamethyldisilazane were added thereto. The reactants were stirred for 2.5 hours at 35 to 40° C., and then cooled to room temperature. After addition of 100 ml of n-hexane, the solution was washed with water and then brine in order. The organic phase was dried over magnesium sulfate and the solvent was concentrated under reduced pressure to give 9.4 g (yield: 100%) of α,α'-bis[2',4"-O-bis(trimethylsilyl)-erythromycin A 9-oxime]-9-O-p-xylene in foam.

$^1$H-NMR for the compound was the same as that of the compound obtained in Example 2.

EXAMPLE 4

25.5 G of α,α'-bis[2',4"-O-bis(trimethylsilyl)erythromycin A 9-oxime]-9-O-p-xylene obtained in Example 2 were dissolved in a mixed solvent of 150 ml of dimethylsulfoxide and 150 ml of tetrahydrofuran and the mixture was then cooed to 0 to 5° C. 1.95 ml of iodomethane and 1.62 g of potassium hydroxide in powder were added thereto, and the reaction mixture was then stirred for 7 hours at the same temperature. After addition of 300 ml of n-hexane, the solution was washed with water and then brine in turn. The organic phase was dried on magnesium sulfate and the solvent was concentrated under reduced pressure to give 23.3 g (yield: 90%) of α,α'-bis[2',4"-O-bis(trimethylsilyl)-6-O-methylerythromycin A 9-oxime]-9-O-p-xylene in foam. The analytical sample was purified by silica gel column chromatography (eluent, hexane/acetone=4/1).

PMR (CDCl$_3$, ppm) δ7.32(s, 4H, —C$_6$H$_4$—), 5.07(dd, 4H, two benzyl —CH$_2$—), 3.30(s, 6H, two cladinose —OCH$_3$), 3.07(s, 6H, 2개의, 6-OCH$_3$), 2.34(s, 12H, two desosamine —N(CH$_3$)$_2$, 0.15(s, 18H, two —Si(CH$_3$)$_3$, 0.08 (s, 18H, two —Si(CH$_3$)$_3$)

EXAMPLE 5

14.0 G of α,α'-bis[2',4"-O-bis(trimethylsilyl)-6-O-methylerythromycin A 9-oxime]-9-O-p-xylene prepared in Example 4 and 2.5 ml of 99% formic acid were dissolved in 100 ml of methanol and the mixture was stirred for 4 hours at 30° C. to 40° C. 100 ml of water were then added thereto. After pH of the solution was adjusted to 9 by adding concentrated aqueous ammonia solution, the solution was extracted twice with 150 ml of ethyl acetate. Organic phases were combined, washed with brine, and then dried over magnesium sulfate. The solvent was concentrated under reduced pressure to give 11.4 g (yield: 96%) of α,α'-bis[6-O-methylerythromycin A 9-oxime]-9-O-p-xylene in foam. This was purified by recrystalization from ethanol, and centrifugation.

PMR (CDCl$_3$, ppm) δ7.33(s, 4H, —C$_6$H$_4$—), 5.04(dd, 4H, two benzyl —CH$_2$—), 3.34(s, 6H, two cladinose —OCH$_3$), 3.09(s, 6H, two 6-OCH$_3$), 2.30(s, 12H, two desosamine —N(CH$_3$)$_2$)

EXAMPLE 6

After 9.7 g of α,α'-bis(6-O-methylerythromycin A 9-oxime)-9-O-p-xylene prepared in Example 5 were dissolved in 120ml of methanol, 1.51 g of ammonium formate, 4.53 ml of formic acid and 1.28 g of 10% palladium-carbon were added thereto in order. The mixture was stirred for 5 hours at 50 to 55° C. and then cooled to room temperature. 150 ml of water were added to the reactants and the pH of the solution was adjusted to 9 by adding concentrated ammonia solution. When solids were formed, water was further added, and the solids were filtered. The solids were washed with water and dried to give 7.0 g (yield: 76%) of 6-O-methylerythromycin A 9-oxime in powder. This was purified by recrystalization from a mixed solvent of ethanol-isopropyl ether.

PMR (CDCl$_3$, ppm) δ5.11(dd, 1H, 13-H), 4.95(d, 1H, 1"-H), 3.34(s, 3H, cladinose —OCH$_3$), 3.11(s, 3H, 6-OCH$_3$), 2.30(s, 6H, desosamine —N(CH$_3$)$_2$)

EXAMPLE 7

2.88 G of α,α'-bis[2',4"-O-bis(trimethylsilyl)-6-O-methylerythromycin A 9-oxime]-O-p-xylene prepared in Example 4 were dissolved in 30 ml of ethanol. 378 mg of ammonium formate, 1.33 ml of 85% formic acid and 320 mg of 10% palladium-carbon were added thereto in order. The mixture was stirred for 5 hours at 50 to 55° C. and then cooled to room temperature. After addition of water and ethyl acetate, the pH of the solution was adjusted to 9 by adding sodium carbonate. Organic phases were combined, washed with water and brine in order and then concentrated to dryness to give 1.95 g(yield: 85%) of crude product of 6-O-methylerythromycin A 9-oxime in foam. The analytical sample was purified by silica gel column chromatography in a mixed solvent of ethanol and isopropanol.

$^1$H-NMR for the compound was the same as that of the compound obtained in Example 6.

EXAMPLE 8

5.3 G of α,α'-bis[6-O-methyerythromycin A 9-oxime]-9-O-p-xylene prepared in Example 5 were dissolved in 60 ml of methanol. 1.23 g of ammonium formate, 4.3 ml of 85% formic acid and 694 mg of 10% palladium-carbon were added thereto in order. The mixture was stirred for 5 hours at 50 to 55° C. After addition of 60 ml of water and 5.44 g of sodium hydrogen sulfite, the reaction solution was refluxed for 7 hours. The solution was cooled to room temperature and filtered through Celite, and 120 ml of water were added. The pH of the solution was adjusted to 9 by adding sodium carbonate. When solids were formed, water was further added and the solids were filtered. The filtrate was washed with water and hexane in order, dried and recrystalized from ethanol to give 3.17 g (yield: 65%) of 6-O-methylerythromycin A in powder. This was purified by recrystalization from ethanol.

PMR (CDCl$_3$, ppm) δ5.06(dd. 1H, 13-H), 4.92(d, 1H, 1"-H), 4.44(d, 1H, 1'-H), 3.33(s, 3H, cladinose —OCH$_3$), 3.03(s, 3H, 6-OCH$_3$), 2.28(s, 6H, desosamine —N(CH$_3$)$_2$), 1.41(s, 3H, 18-H), 0.85(t, 3H, 15-H)

EXAMPLE 9

1.92 G of α,α'-bis[2',4"-O-bis(trimethylsilyl)-6-O-methylerythromycin A 9-oxime]-9-O-p-xylene prepared in Example 4 were dissolved in 20 ml of ethanol. 378 mg of ammonium formate, 1.33 ml of 85% formic acid and 213 mg of 10% palladium-carbon were added thereto in order. The mixture was stirred for 5 hours at 50 to 55° C. After addition of 20 ml of water and 1.67 g of sodium hydrogen sulfite, the reaction solution was refluxed for 7 hours. The solution was cooled to room temperature, and filtered through Celite, and water and ethyl acetate were added thereto. The pH of the solution was adjusted to 9 by adding sodium carbonate. The organic phase was separated and the water phase was extracted with ethyl acetate. The organic phases were combined, washed with water and brine in order, and then concentrated over sodium sulfate to dryness to give a crude product in white foam which was recrystallized from ethanol to give 0.9 g (yield: 60%) of 6-O-methyl erythromycin A in white solids.

$^1$H-NMR for the compound was the same as that of the compound obtained in Example 8.

INDUSTRIAL APPLICABILITY

The present invention provides a process for efficiently preparing 6-O-alkyl erythromycin A of formula (II) and its oxime which comprises concurrently protecting two molecules of the hydroxy groups of erythromycin A 9-oxime with one molecule of protecting group using protecting groups which can react with oxime at the two positions to give an erythromycin A 9-oxime compound in symmetric structure; protecting up to four hydroxy groups of erythromycin A 9-oxime compound corresponding to the 2' and 4" positions of erythromycin A with silyl protecting groups; and selectively alkylating the hydroxy group at the 6 position; and then carrying out deprotection and deoximation. The present invention further provides a process for preparing erythromycin A 9-oxime compound represented by the formula (I) and 6-O-alkyl erythromycin a represented by the formula (II) and its oxime wherein a number of reaction steps are carried out step by step, or two or more steps are consecutively or concurrently carried out without isolating the desired product obtained in each step therefore, according to the present invention, it is possible to prepare 6-O-alkyl erythromycin A represented by the formula (II) which is clinically effective in treating various infections in a high yield with a low expense by lowering the cost for the oxime protecting groups.

What is claimed is:

1. A process for preparing 6-O-alkyl erythromycin A 9-oxime and 6-O-alkyl erythromycin A represented by the following formula (II) which comprises the steps (a) to (e):

(a) reacting erythromycin A 9-oxime represented by the following formula (III) with a bifunctional linker represented by the following formula (IV) to give an erythromycin A 9-oxime compound represented by the following formula (V);

(b) silylating the erythromycin A 9-oxime compound of formula (V) obtained in the step (a) to give an erythromycin A 9-oxime compound represented by the following formula (VI);

(c) alkylating the compound of formula (VI) obtained in the step (b) to give an erythromycin A 9-oxime compound represented by the following formula (VII);

(d) desilylating the erythromycin A 9-oxime compound of formula (VII) obtained in step (c) to give an erythromycin A 9-oxime compound represented by the following formula (VIII); and (e) removing the oxime protecting group of the compound of formula (VIII) obtained in the step (d) or consecutively carrying out removal of the oxime protecting group and deoximation reaction:

(II)
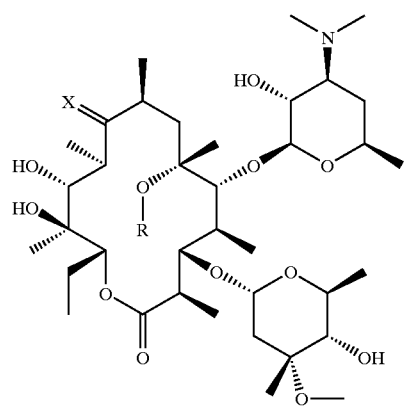
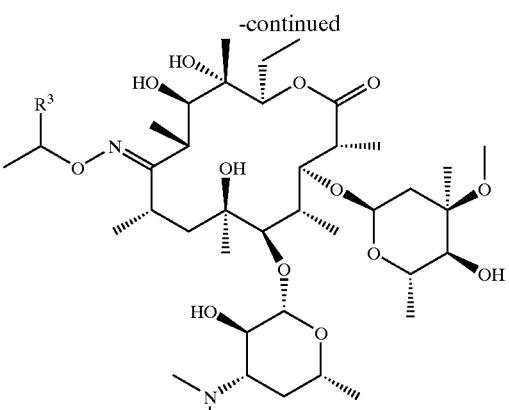
-continued
(III)
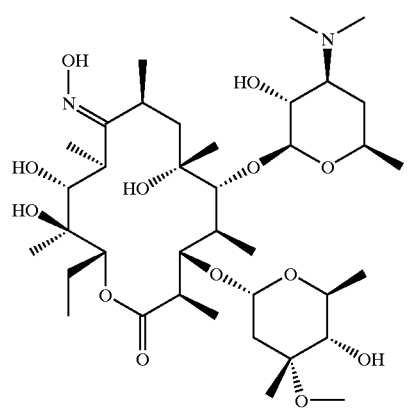
(VI)
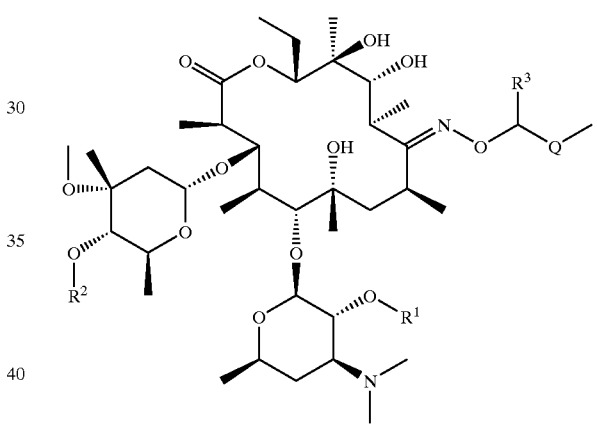
(IV)
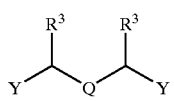
(V)
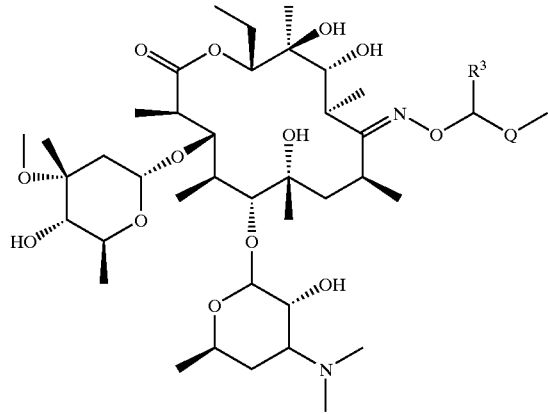
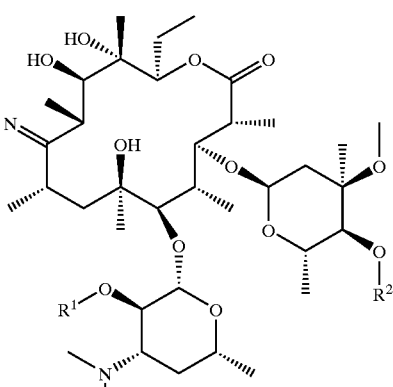

21
-continued (VII)

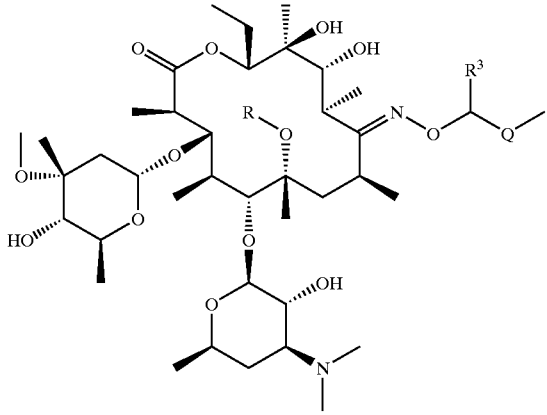

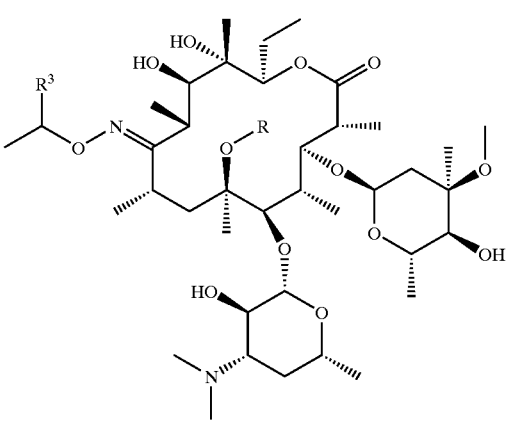

(VIII)

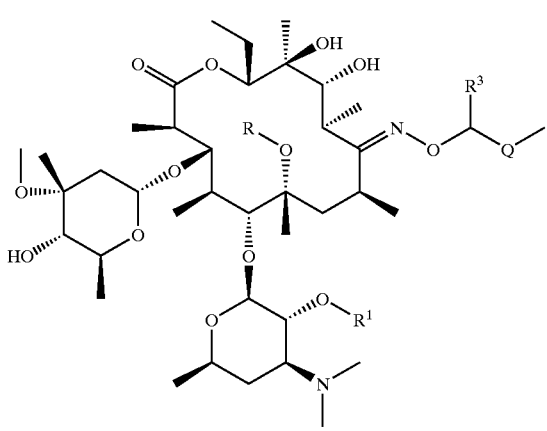

22
-continued

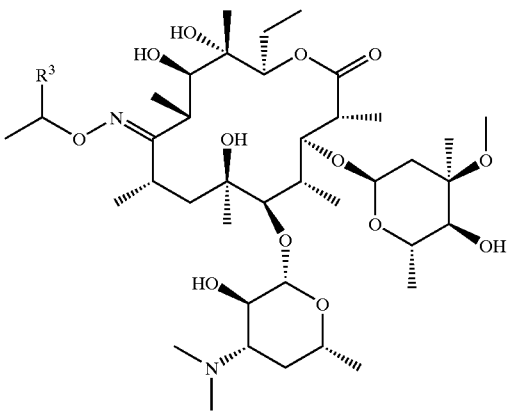

wherein,

R represents a $C_{1-3}$ alkyl group;

$R^1$ and $R^2$ each independently represents a silyl group represented by $—SiR^4R^5R^6$ in which $R^4$, $R^5$, and $R^6$ each independently represents a $C_{1-6}$ alkyl group, a $C_{1-3}$ alkyl group substituted with a phenyl group, a phenyl group, a $C_{5-7}$ cycloalkyl group, or a $C_{2-5}$ alkenyl group; or $R^2$ represents hydrogen;

$R^3$ represents hydrogen, a 1-alkenyl group, or an aryl group;

Q represents a cis- or trans-alkenylene group represented by $—(CH=CH)_m—$, a α,ω-dienylene group represented by $—[CH=CH—(CH2)_m—CH=CH]—$, a phenyl group consisting of ortho-, meta- or para-, an arylene group or an alkylene group represented by $—(CH_2)_n—$ when $R^3$ represents a 1-alkenyl group or an aryl group, m is an integer of 1 to 3, and n is an integer of 1 to 10, wherein one or more carbons in the above alkylene group, alkenylene group, dienylene group or arylene group may be substituted with an alkyl substituent;

X represents O or N—OH; and

Y represents chloride, bromide, iodide, mesylate, tosylate, or triflate.

2. The process according to claim 1, in which Q represents a 1,2-diphenylethyl group, a phenyl group consisting of ortho-, meta- or para-, a 1,4-naphthalenyl group, a cis- or trans-ethylene group or a butadienyl group; R represents hydrogen or a methyl group; $R^1$ represents a trimethyl silyl group, $R^2$ represents hydrogen or a trimethylsilyl group; and $R^3$ represents hydrogen.

3. The process according to claim, 1, in which Q represents a para-phenyl group; R represents a methyl group; $R^1$ represents a trimethylsilyl group, $R^2$ represents hydrogen or trimethylsilyl group; and $R^3$ represents hydrogen.

4. The process according to claim 1, in which the alkylating agent in step (c) is selected from the group consisting of methyl bromide, methyl iodide, ethyl bromide, ethyl bromide, ethyl iodide, propyl bromide, propyl iodide, allyl bromide, dimethyl sulfate, p-toluenesulfonylmethane, and methanesulfonylmethane.-

5. The process according to claim 1, in which the alkylating agent in step (c) is used in an amount of about 2 to 4 mole equivalents with respect to the compound of formula (VI).

6. The process according to claim 1, in which the alkylating agent and the compound of formula (VI) is reacted at temperature of about −15° C. to 40° C. under the presence of a base and a solvent.

7. The process according to claim 5, which is done in the presence of a solvent, wherein the solvent is selected from the group consisting of N,N-dimethylformamide, N,N-dimethylacetamide, N-methyl-2-pyrolidone, di-methyl sulfoxide, N,N,N',N',N'',N''-hexamethylphosphoramide, and the mixture thereof or a mixed solvent consisting of one solvent selected from the above solvent and another solvent selected from the group consisting of tetrahydrofurane, 1,2-dimethoxyetliane, dioxane, and acetonitrile.

8. The process according to claim 5, which is done in the presence of a base, wherein the base is selected from the group consisting of sodium hydride, potassium hydride, sodium hydroxide, potassium hydroxide, and potassium t-butoxide.

9. The process according to claim 5, which is done in the presence of a base, wherein the base is used in an amount of about 2 to 4 mole equivalents with respect to the compound of formula (VI).

10. Erythromycin A 9-oxime compound represented by the following formula (I) which can be used as an intermediate for the manufacture of 6-O-alkyl erythromycin A 9-oxime and 6-O-alkyl erythromycin A represented by the formula (II) as defined in claim 1

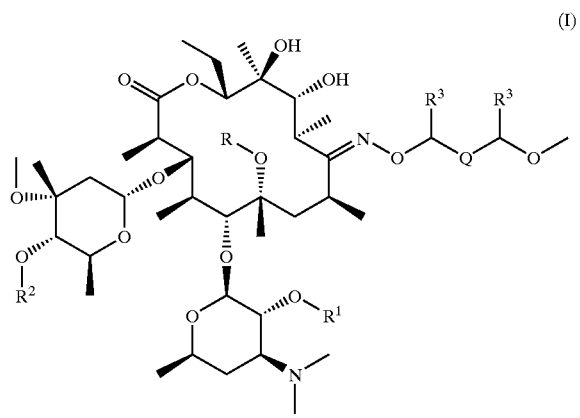

(I)

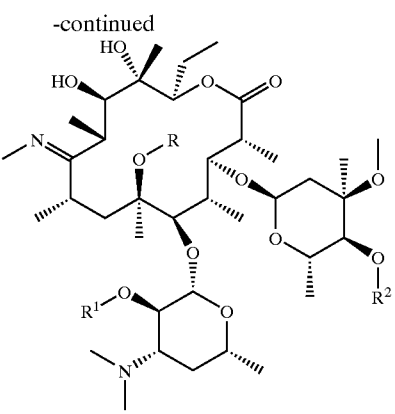

wherein,
R represents hydrogen, or a $C_{1-6}$ alkyl group,
$R^1$ and $R^2$ each independently represents hydrogen or a silyl group represented by —$SiR^4R^5R^6$ in which $R^4$, $R^5$, and $R^6$ each independently represents a $C_{1-6}$ alkyl group, a $C_{1-3}$ alkyl group substituted with a phenyl group, a phenyl group, a $C_{5-7}$ cycloalkyl group, or a $C_{2-5}$ alkenyl group; or $R^3$ represents hydrogen, a 1-alkenyl group, or an aryl-group;
Q represents a cis- or trans-alkenylene group represented by —(CH=CH)$_m$—, a α,ω-dienylene group represented by —[CH=CH—(CH2)$_m$—CH=CH]—, a phenyl group consisting of ortho-, meta- or para-, an arylene group or an alkylene group represented by —(CH$_2$)$_n$— when $R^3$ represents a 1-alkenyl group or an aryl group, m is an integer of 1 to 3, and n is an integer of 1 to 10, wherein one or more carbons in the above alkylene group, alkenylene group, dienylene group or arylene group may be substituted with an alkyl substituent.

11. The compound according to claim 10, in which Q represents a 1,2-diphenylethyl group, a phenyl group consisting of ortho-, meta- or para-, a 1,4-naphthalenyl group, a cis- or trans-ethylene group or a butadienyl group; R represents hydrogen or a methyl group; $R^1$ represents a trimethyl silyl group, $R^2$ represents hydrogen or a trimethylsilyl group; and $R^3$ represents hydrogen.

12. The compound according to claim 10, in which Q represents a para-phenyl group; R represents a methyl group; $R^1$ represents a trimethylsilyl group, $R^2$ represents hydrogen or trimethylsilyl group; and $R^3$ represents hydrogen.

13. The process according to claim 1, wherein the arylene group is a naphthalenyl, an anthracenyl or a pylidinyl group.

14. The compound according to claim 10, wherein the arylene group is a naphthalenyl, an anthracenyl or a pylidinyl group.

* * * * *